(12) United States Patent
Whelan

(10) Patent No.: US 10,792,120 B2
(45) Date of Patent: Oct. 6, 2020

(54) MEDICAL QUIVER

(71) Applicant: Chris Whelan, Leichhardt (AU)

(72) Inventor: Chris Whelan, Leichhardt (AU)

(73) Assignee: NOBLE HOUSE GROUP PTY. LTD. (AU)

( * ) Notice: Subject to any disclaimer, the term of this patent is extended or adjusted under 35 U.S.C. 154(b) by 0 days.

(21) Appl. No.: 15/566,232

(22) PCT Filed: Apr. 14, 2016

(86) PCT No.: PCT/AU2016/000128
§ 371 (c)(1),
(2) Date: Oct. 13, 2017

(87) PCT Pub. No.: WO2016/164962
PCT Pub. Date: Oct. 20, 2016

(65) Prior Publication Data
US 2018/0333216 A1    Nov. 22, 2018

Related U.S. Application Data

(60) Provisional application No. 62/146,994, filed on Apr. 14, 2015.

(51) Int. Cl.
*A61B 50/30*        (2016.01)
*A61B 17/00*        (2006.01)
*F41B 5/06*         (2006.01)

(52) U.S. Cl.
CPC ........ *A61B 50/30* (2016.02); *A61B 17/00234* (2013.01); *A61B 2017/00292* (2013.01); *A61B 2017/00991* (2013.01); *F41B 5/06* (2013.01)

(58) Field of Classification Search
CPC .............. A61B 50/30; A61B 17/00234; A61B 2017/00292; A61B 2017/00991;
(Continued)

(56) References Cited

U.S. PATENT DOCUMENTS 3,514,008 A * 5/1970 Dorn ..................... A61J 7/0046
                                                   206/218
5,061,246 A    10/1991 Anapliotis
(Continued)

FOREIGN PATENT DOCUMENTS

EP           1374942        1/2004
WO    WO 2015/047455        4/2015

OTHER PUBLICATIONS

Diathermy quiver: downloaded from the internet Jul. 12, 2016. <URL http://web.archive.org/web/20151210034051 /http:i/www.phoenixsurgical.co.uki shop/diathermy-quiver-telescopic60mm-dia-extending-400mm-ph757561 > Published online Dec. 10, 2015 as per Wayback Machine.

(Continued)

*Primary Examiner* — Chun Hoi Cheung
(74) *Attorney, Agent, or Firm* — Galbreath Law Offices, P.C.; John A. Galbreath

(57) ABSTRACT

A collapsible quiver (2) has an outer tube (4) and an inner tube (6). When extended the inner end (24) of the inner tube (4) engages the inner surface of the outer tube (6) so there is substantially no discontinuity of the inner surface defined by the first and second tubular members.

19 Claims, 7 Drawing Sheets

(58) Field of Classification Search
CPC ... A61B 50/31; A61B 50/00; A61B 17/06114; F41B 5/06; B65D 21/08; B65D 41/00; B65D 83/10; B65D 73/00; B65D 5/5028; B65D 21/086; B65D 25/56; B65D 41/005; B65D 85/72
USPC .............. 206/363, 482, 317, 315.1, 315.11; 220/666, 8, 218, 144
See application file for complete search history.

(56) References Cited

U.S. PATENT DOCUMENTS

| | | | | |
|---|---|---|---|---|
| 5,829,591 | A * | 11/1998 | Lyons | B65D 21/086 206/373 |
| 6,077,074 | A | 6/2000 | Homra | |
| 7,252,204 | B1 * | 8/2007 | Small | B65D 55/145 206/459.5 |
| 9,745,085 | B2 * | 8/2017 | Pawlowski | B65B 3/04 |
| 2003/0024928 | A1 * | 2/2003 | Serden | E04B 1/34305 220/4.04 |
| 2004/0232016 | A1 * | 11/2004 | Dietrich | A63B 55/404 206/315.3 |
| 2005/0230280 | A1 * | 10/2005 | Sotiropolous | A61B 90/50 206/363 |
| 2006/0020165 | A1 | 1/2006 | Adams | |
| 2012/0228289 | A1 * | 9/2012 | Boyles | A01K 97/08 220/8 |
| 2015/0253055 | A1 * | 9/2015 | Tsui | B65D 21/086 62/62 |
| 2015/0344180 | A1 * | 12/2015 | Shakoori Divani | B65D 21/086 206/459.1 |

OTHER PUBLICATIONS

Surgical telescopic quiver: Downloaded from the internet Jul. 12, 2016. <URL https://www.ga2medical.com/index.php/about/custom-oem-manufacturingiplatinumsurgical-telescopic-quiver Online publication date not available.

Telescopic archery quiver: Downloaded from the internet Jul. 12, 2016. <URL http://g02.A.aliedn.com/kt71 ITB IZEXv1IVXXXXXIXXXXg6xXPXXXr/UtilityAdjustable-PE-UN-Arrow-Case-Quiver-Shoulder-Tube-Telescopic-Drawing-Tube.jpg> Online publication date not available.

Single Use Laparascopic Telescopic Quiver: downloaded from the internet Dec. 17, 2014. <URL http://www.advmedical.com/products/197-quivers.aspx Online publication date not available.

Constar is the Exclusive Manufacturer: downloaded from the internet Dec. 17, 2014. <URL http://www.constar.com.au/links/ Online publication date not available.

Telescopic Diathermy Quiver. Inka Surgical Instruments, Copyright 2014. Online publication date not available.

* cited by examiner

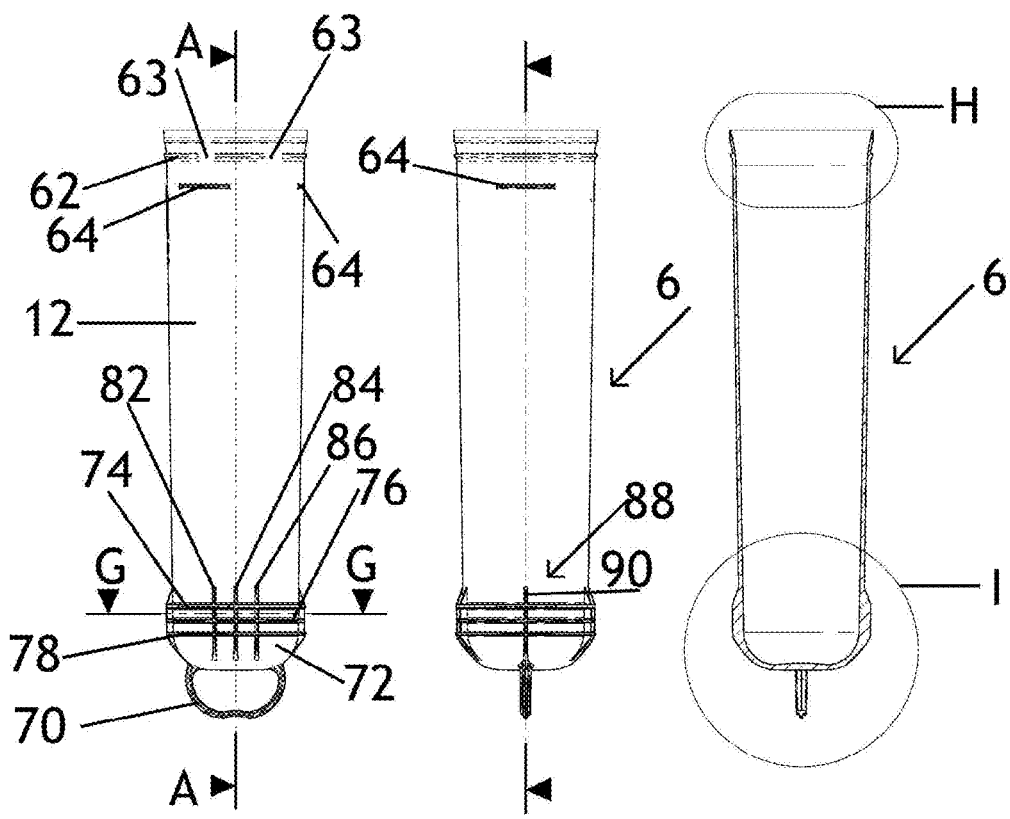
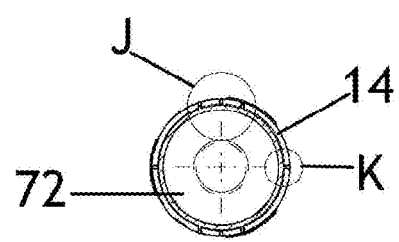
Figure 10  Figure 11  Figure 12
Figure 12 A

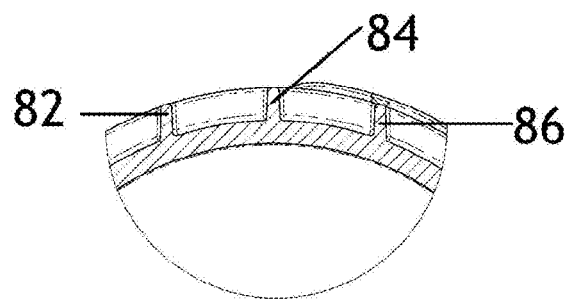
Figure 13
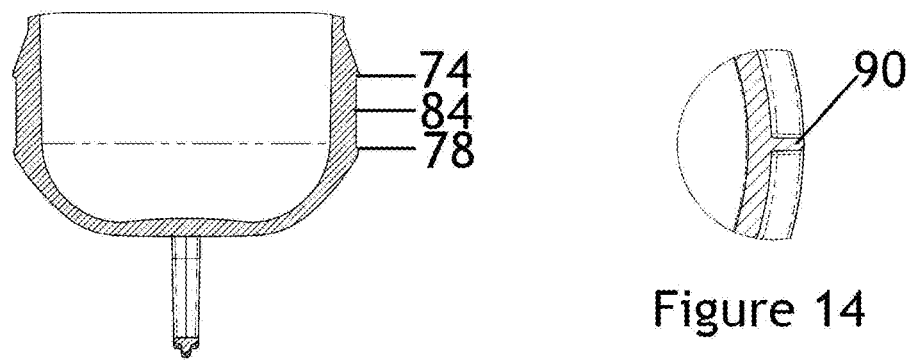
Figure 15
Figure 14
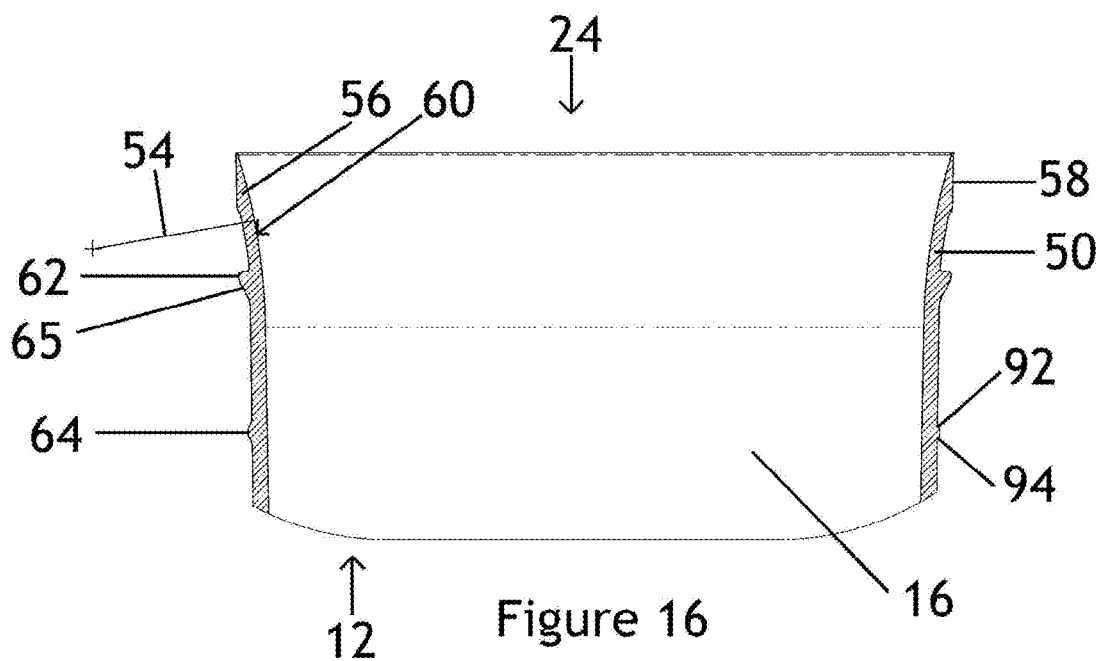
Figure 16

MEDICAL QUIVER

TECHNICAL FIELD

This invention related to receptacles for medical devices and more particularly to receptacles, commonly called quivers, for long medical devices, such as laparoscopes and the like.

BACKGROUND ART

Quivers are receptacles for receiving elongate medical devices, such as laparoscopes. Typically they are used for temporarily storing the device during an operation. The device may be inserted and retrieved a number of times.

To reduce package size during transport and storage some medical quivers are collapsible, with two or more tubes arranged end on end to be telescopically collapsible, with an outer end of one tube located within the inner end of an outer tube.

Current telescopic quivers typically have an overlapping annular lip arrangement, with the inner end of the inner tube 6 having radially inwards directed annular flange that overlaps a radially outwards directed annular flange that extends from the outer end of the inner tube 18. Whilst this is a simple arrangement it creates a step or discontinuity in the inner wall surface(s) or the two tubes at their junction. Inserting a medical device into such a quiver can result in the device catching on this step or discontinuity.

DISCLOSURE OF THE INVENTION

In a broad form the invention provides a collapsible quiver comprising
  at least two elongate tubular members, comprising a first elongate tubular member and a second elongate tubular member;
  the first member having a first open end;
  at least a part of the second member received within the first member for reciprocal motion in the elongate direction relative to the first member from a retracted position to an extended position in which at least a first end portion of the second member extends out of the first open end;
  the second member having a second end portion at a second end thereof that, in the extended position, engages the inner surface of the first member and which is shaped so that, in the extended position, at the junction of the second end with the first member there is substantially no discontinuity of the inner surface defined by the first and second tubular members.

The second end portion preferably has a first inner surface portion of its inner surface and a second outer surface portion of its outer surface that converge toward second end.

The second member may have a central portion between its first and second ends. The internal area of central portion preferably reduces from the second end to the first end.

In one form the second outer surface portion extends alongside the inner surface of the first member and the first inner surface portion extends toward the outer surface. In cross section the first inner surface portion may be curved. Preferably the first inner surface portion extends from a second inner surface portion of the inner surface. Preferably the first inner surface portion extends tangent to the second inner surface portion.

Preferably the second outer surface portion engages the inner surface of the first member when the device is in the extended position to provide a seal that resists passage of fluid between the first and second members. More preferably the second portion is sized so that the first member applies a compressive force to the second member when in the extended portion. Where the first and second members have a circular cross section, the outside diameter of the second member may be greater than the inside diameter of the adjacent inside surface of the first member.

The inside surface of the first member and the outside surface of the second member may be shaped so that movement of the second member out of the first member brings the outside surface of the second member and the inside surface of the first member into engagement or into closer engagement with each other.

Where the inner surface of the first member and the outer surface of the second member have cross sectional shapes that are substantially the same along the longitudinal direction, the shapes may be tapered toward the first end. Where these shapes are circular, the tubes may be tapered to each define a cone or a truncated cone.

The first end of the second member is preferably closed.

The first member may have an intermediate portion between its first and second ends. The internal area of an intermediate portion preferably reduces from the second to the first end.

The first end portion of the first member preferably includes a free end portion that has a cross sectional area less than the cross sectional area of the adjacent an intermediate portion. Preferably the cross sectional shape of the first member is substantially constant with the area changing. Where the first member has a circular cross section, the free end portion of the first member may have a smaller diameter or radius compared to the intermediate portion.

Preferably the free end portion of the first member is connected to the adjacent intermediate portion by a transition portion.

The second end portion of the second member preferably has first and second retaining portions. The first and second retaining portions are sized so that, the size of the normal area of the free end portion prevents their passage through the free end portion of the first member. The first retaining portion is sized to pass through the reduced area free end portion of the first member by deflection of at least a part of the free end portion of the first member. The second retaining portion is sized such that, in normal use, it will not pass through the reduced area free end portion.

Preferably the first and second retaining portions each comprises at least one protrusion extending from the outer surface of the second member. Preferably the first retaining portion comprises at least two discontinuous protrusions.

Preferably the second retaining portion comprises at least one continuous protrusion.

Preferably there is at least one slot extending longitudinally in at least one or both of the free end portion and the transition portion of the first member. Where the first member includes at least one slot, at least one slot may extend into the adjacent intermediate portion. Where the first member includes at least one slot, preferably at least one slot extends from the free end of the free end portion so as to define at least one finger.

The at least one slot allows for the first member to increase or change its internal area in the region of the respective slot. Where the at least one slot is in the at least the free end portion this allows the free end portion to increase or change its internal the area. Where the at least one slot extends from the free end of the free end portion so as to define at least one finger, this allows the at least one finger to move. Where the free end portion has a circular cross section preferably the at least one finger is deflectable radially outwards.

The first and second retaining portions are preferably spaced so that the second retaining portion is adjacent the transition portion and the first portion is outside the first member adjacent the free end.

Where the first and second members are circular in cross section, preferably the first and second retaining portions extend radially more than at least the reduced area free end portion but less than the intermediate portion of the first member. The first retaining portion preferably extends radially less than the second retaining portion.

BRIEF DESCRIPTION OF THE DRAWINGS

FIG. 10 is a side view of the inner tube of the quiver of FIG. 1.

FIG. 11 is a side view of the inner tube of the quiver of FIG. 1 at 90 degrees to FIG. 10.

FIG. 12 is a sectional view of the inner tube of FIG. 10 taken along line AA in FIG. 10.

FIG. 12a is a cross sectional view of the inner tube of FIG. 10 taken along line GG in FIG. 10.

FIG. 13 is a detail cross sectional view of a part of the inner tube of FIG. 12a circled J in FIG. 12a.

FIG. 14 is a detail cross sectional view of another part of the inner tube of FIG. 12a circled K in FIG. 12a.

FIG. 15 is a detail cross sectional view of the closed end of inner tube of FIG. 10 circled I in FIG. 12.

FIG. 16 is a detail cross sectional view of the open end of inner tube of FIG. 10 circled H in FIG. 12.

BEST MODE OF CARRYING OUT THE INVENTION

Figure 1:
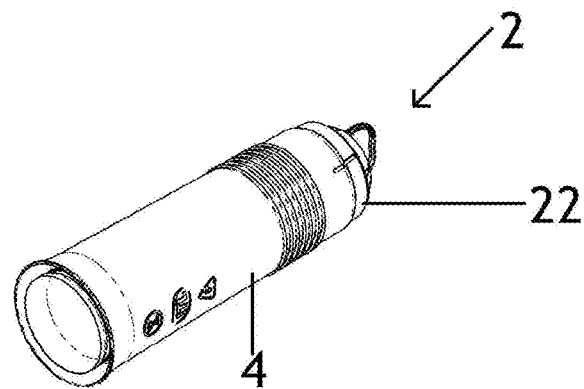
FIG. 1 is a perspective view of a quiver according to a first embodiment of the invention a collapsed state.
Figure 2:
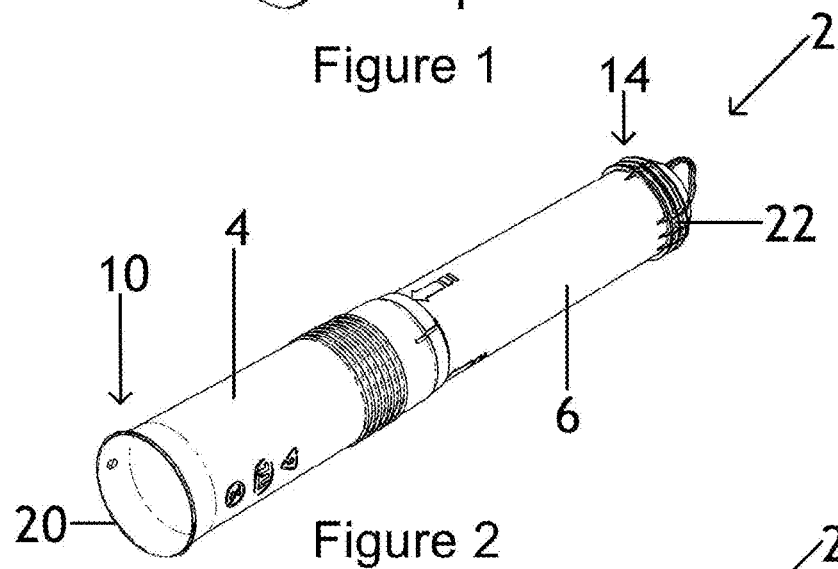
FIG. 2 is a perspective view of the quiver of FIG. 1 in an extended state.
Figure 3:
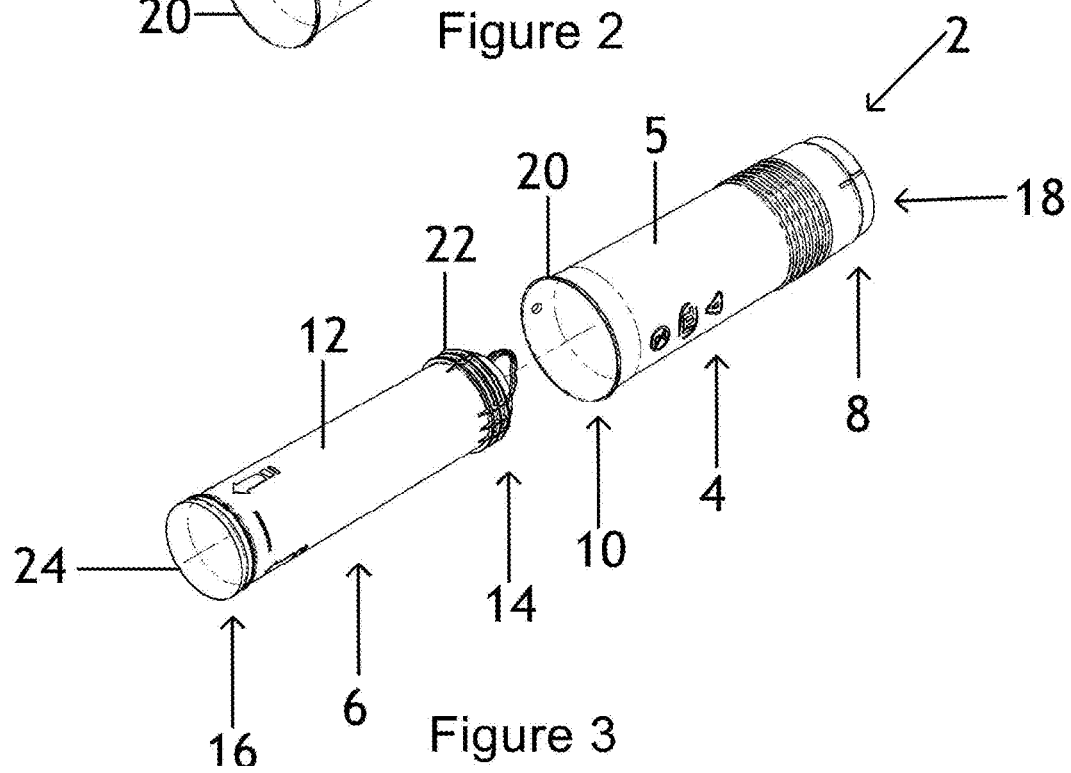
FIG. 3 is an exploded perspective view of the quiver of FIG. 1.

Referring to FIGS. 1 to 17 there is shown a collapsible quiver 2. The quiver 2 comprises an outer tube 4 and an inner tube 6. The outer tube 4 has central portion 5 and end portions 8 and 10. The inner tube 6 has central portion 12 and end portions 14 and 16.

The ends 18 and 20 of outer tube 4 are open and the outer tube 4 is sized to receive the inner tube 6 within it itself. The inner tube 6 is sized to fit into the outer tube 4 via the end 20. In this embodiment the quiver 2 only comprises the two tubes 4, 6 and the end 22 of inner tube 6 is closed with all other ends being open. However, if three or more tubes were used all except one tube at one end of the telescoping set of tubes would be open at both ends. In this embodiment the tubes 4 and 6 have substantially continuous side walls 11 with no apertures in the side walls. It will be appreciated that continuous side walls are not essential and, if appropriate, apertures may be provided in the side walls for purposes such as material reduction.

Figure 4:
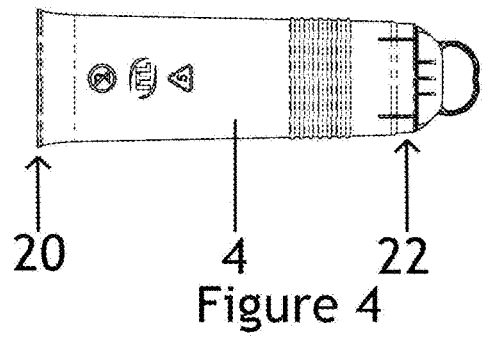
FIG. 4 is a side view of the quiver of FIG. 1 in a collapsed state.
Figure 5:
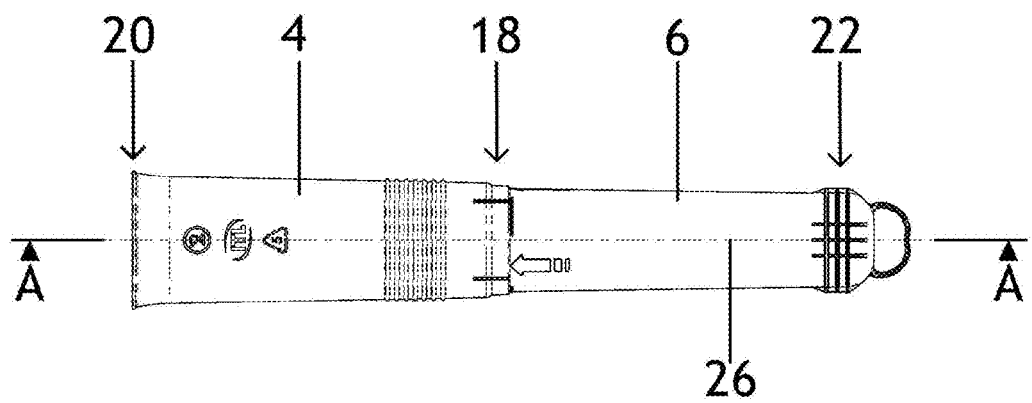
FIG. 5 is a side view of the quiver of FIG. 1 in an extended state.
Figure 6:
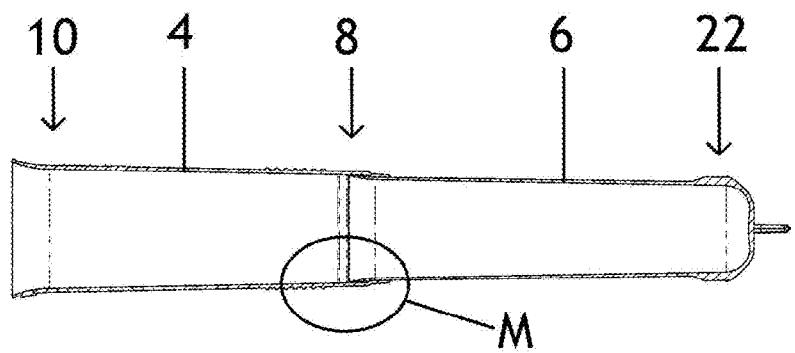
FIG. 6 is a sectional view of the quiver of FIG. 5 taken along line AA.

As best seen in FIGS. 1 and 4 the two tubes 4, 6 are of similar lengths and when the end 24 of inner tube 6 has passed into outer tube 4, the end 22 extends out of end 18.

The end portion 10 is flared outwards to assist insertion of the tube 6 into tube 4 and also, in use, to aid insertion of a medical device into the quiver.

The tubes 4 and 6 have a generally circular cross-section and the central sections 5 and 12 are both tapered towards ends 8 and 14, respectively, so the central sections are of a slightly smaller diameter towards ends 8 and 14 compared to the diameter nearer ends 10 and 16. This aids in insertion of the inner tube 6 into the outer tube 4 and subsequent extension. In the preferred embodiment the taper is about 1 degree to the longitudinal axis 26.

Figure 7:
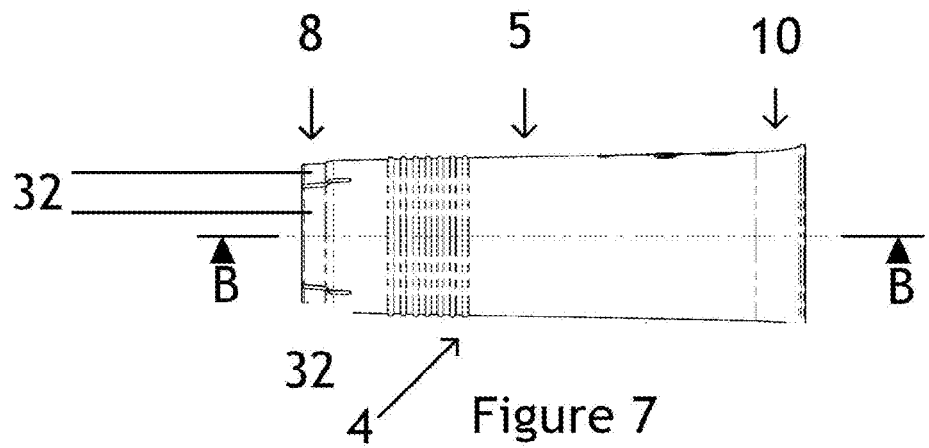
FIG. 7 is a side view of the outer tube of the quiver of FIG. 1.
Figure 8:
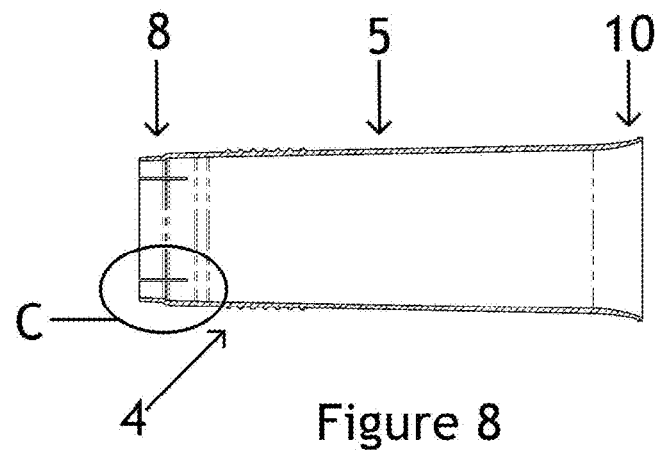
FIG. 8 is a sectional view of the outer tube of FIG. 7 taken along line BB.
Figure 9:
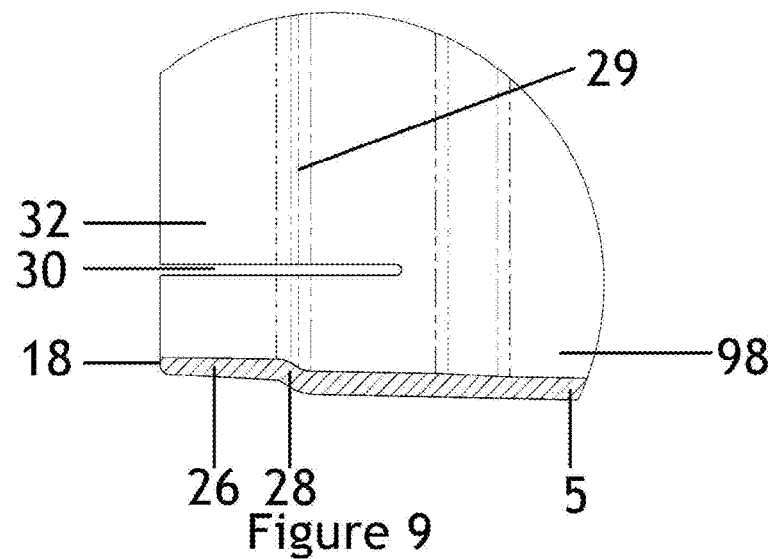
FIG. 9 is a detail perspective view of a part of the outer tube of FIG. 7 circled C in FIG. 7.

As best seen in FIGS. 7, 8 and 9 the end portion 8 of the tube 4 comprises a free end portion 26 having a reduced diameter compared to the adjacent central portion 5 of the tube 12. The free end portion 26 and adjacent central portion 5 are joined by an angled or curved step portion 28.

A plurality of slots 30 extend axially from the free end 18 of the free end portion 26 and are spaced around the circumference. These slots 30 extend axially through the step portion 28 and into the central portion 5 and so define a plurality of fingers 32, which may flex radially relative to the central portion 5. In the embodiment shown there are five slots 30 but there may be more or less, including a single slot. Functionally the slots are more effective if they extend into the transition portion 28 and even more effective if they also extend into the central portion 5, but this not critical. Further, as the function is to enable the free end portion 26 and/or the transition portion 28 to more easily flex outwards, whilst not preferred, the slots themselves may be omitted.

In the embodiment shown the inner diameter of the free end portion 26 is about 4 to 5% less than the inner diameter of the central portion 5 adjacent to transition portion 28. In this embodiment the wall thickness of the free end portion 26 is slightly less than the wall thickness of central portion 5. However, a tube with a substantially constant wall thickness in that end region may be used.

Referring to FIGS. 10 to 16 the inner tube 6 has a central tapered portion 12, a flared upper portion 16 and a closed portion 14. The central portion 12 is generally circular in cross-section with the wall tapered at about 1 degree to the axis 46.

As best seen in FIG. 16, the flared upper portion 16 has wall portion 50 that increases in diameter toward the open end 24. In the embodiment shown the inner surface 60 of wall portion 50, in cross-section, is curved. In the embodiment shown the inner surface of the wall portion 50 has a radius of curvature 54. However the inner surface of the wall portion 50 could, in cross-section, be straight, i.e. a frusto-conical annular wall; a portion of a cone.

The wall of the inner tube 6 is of a generally constant thickness but toward the open end 16 it reduces in thickness.

In the embodiment shown there is an upper wall portion 56 that has an outer surface 58 that is angled to the inner surface 60 so that the wall thickness reduces toward the end 24 and becomes, in cross-section, substantially a point. It will be appreciated that in practice the end may be rounded or have some thickness. However, relative to the diameter of the tube and/or the size of the medical instrument(s) that the quiver will be used with the end is effectively a point or edge.

The outer surface 58 and inner surface 98 (see FIG. 9) of the wall of the central portion 5 of tube 4 adjacent the step portion 28 are preferably angled to the axis 26 by similar amount. Thus, if the inner wall of outer tube 4 adjacent the step portion 28 is angled at about 1 degree to the axis, the outer surface 58 would also be at about 1 degree to the axis.

The tube 6 has two outwardly extending annular ribs 62 and 64 located near or on the portion 16. In the embodiment shown upper rib 62 is located on portion 16 and lower rib 64 is located on central portion 12. Both ribs may be located on portion 16 or central portion 12.

In the embodiment shown the lower rib 64 is not continuous (see FIGS. 10 and 11) and is formed of two diametrically opposed arcs 66 and 68. The lower rib 64 may be continuous or may be formed of a single arc, (i.e. an incomplete circle) or more than two arcs.

In the embodiment shown the upper rib 62 is a continuous closed ring but may be formed with one or more optional gaps, so as to define a single arc, (i.e. an incomplete circle) or a plurality of arcs. Numerals 63 schematically indicate optional gaps. The location of such optional gaps 63 is not limited to the locations shown.

The other end portion 14 is closed and has loop 70 extending from end wall 72. Loop 70 aids in pulling inner tube 6 out from outer tube 4 to the extended position but may be omitted.

The side wall 73 of end portion 14 has three axially spaced annular ribs 74, 76 and 78. These may have a circular periphery (i.e. extend the same amount at all circumferential locations) or may be non circular (i.e. extend different amounts depending on circumferential locations).

Two sets of diametrically opposed radially spaced axially extending ribs 80 are provided that intersect ribs 74, 76 and 78. In the embodiment shown each set of ribs 80 comprises three ribs 82, 84 and 86. As best seen in FIG. 13 these extend parallel to each other but may extend radially. A second set 88 of diametrically opposed radially spaced axially extending ribs are provided that also intersect ribs 74, 76 and 78. In the embodiment shown there is one pair of ribs 90 (see FIGS. 11 and 14) to each set 88. The ribs 90 are located 90 degrees circumferentially from the centre rib 84 of each set 80.

As seen in FIG. 15, the lowermost rib 78 has a larger diameter than uppermost rib 74, both diameters being larger than that of centre rib 76 and also extending radially more than axial rib sets 80 and 88 where they intersect.

Axially extending rib sets 80 extend radially more than axially extending rib sets 88.

After initial manufacture of the two tubes 4, 6, the end 22 of inner tube 6 is inserted into the open end 20 of outer tube 4 until closed portion 14 partially passes through reduced diameter free end portion 26. The ribs 74, 78, 88 extend radially more than the inner diameter of reduced portion 24 and so cause the fingers 32 to flex radially outwards to allow passage.

The separation between ribs 74 and 78 is slightly greater than the length of the free end portion 26 of outer tube 4. This separation is such that the lower rib 78 may pass through the end 8 to lie outside the outer tube 4 whilst upper rib 74 is still located within the outer tube 4, above stepped portion 28. The fingers 32 may then return radially inwards and lie between ribs 74 and 78. Inner rib 78 resists movement of inner tube toward end 20 (i.e. upwards) whilst outer rib 74 resists movement of inner tube away from end 20 (i.e. downwards). The assembled device 10 thus tends to remain in this compact configuration until actively extended.

When the device 10 needs to be used, a user merely grasps the outer tube 4 and pulls on loop 70 to pull inner tube 6 away from end 20. The fingers flex 32 outwards and allow rib 74 to pass out of the free end portion 26. The inner tube is withdrawn until rib 64 reaches the fingers 32. The fingers 32 flex outwards to allow the rib 64 to pass through. The use of two discontinuous arcs allows the free end portion to distort slightly from a circular shape to allow passage of the rib 64 more easily than if it were a single continuous rib. The upper rib 62 is located so that it is adjacent or in contact with the transition portion 28 just as the lower rib 64 clears the fingers 32. The fingers thus snap back behind rib 64. The lower surface 65 of rib 62 is preferably chosen to match the transition surface 29 of transition portion 28. In cross section the surface 65 has a radius of curvature but may be planar The upper rib 62 extends radially more than lower rib 64 and so would require the fingers 32 to flex outwards more to allow passage than for lower rib 64. Further, as the rib 62 is substantially continuous all portions of the free end would need to deflect outwards simultaneously. The dimensions are chosen so that upper rib 62 will not pass transition portion 28 without application of excessive force. The device is thus temporarily locked with the tubes 4 and 6 in the extended position. Accordingly, a user merely pulls on the inner tube until it snaps and locks in its extended position.

Figure 17:
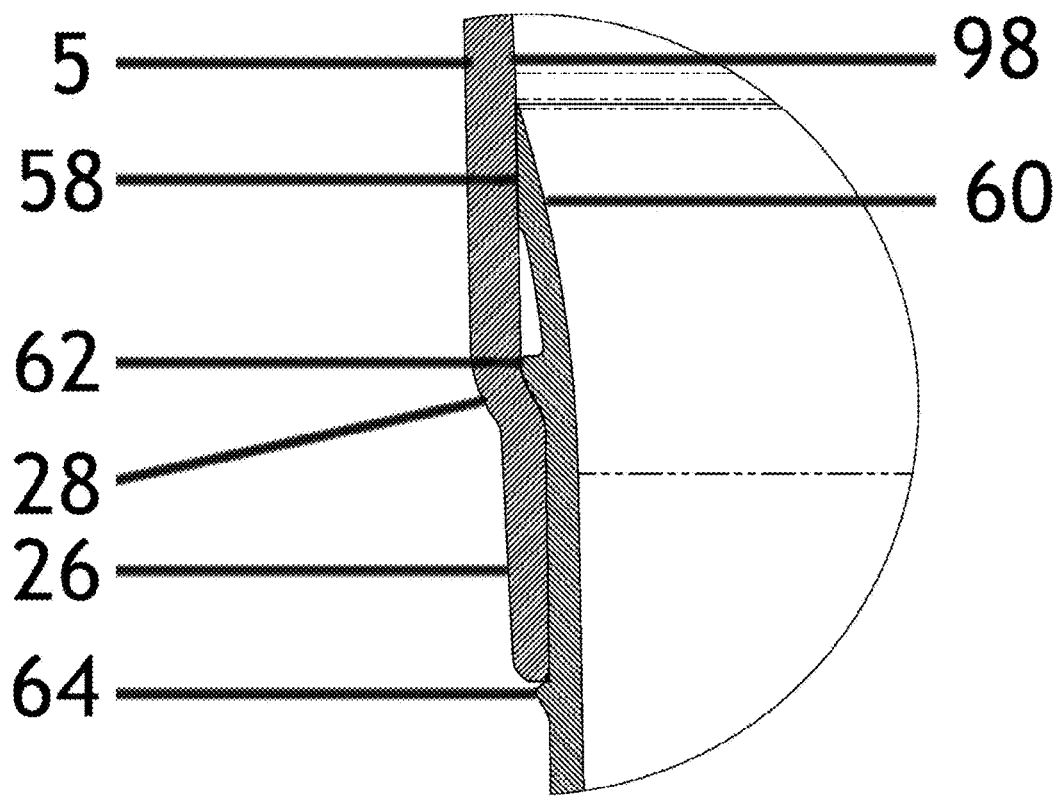
FIG. 17 is a detail cross sectional view of the junction of the inner and outer tubes in the extended position of FIG. 6 circled M in FIG. 6.

In this extended position the end 24 of flared portion 16 of inner tube 6 is located within the outer tube 4 just above the stepped portion 28. The diameter of portion 16 is chosen so that the outer surface 58 is either bearing against the inner surface 98 of tube 4 at that location or is very close to the inner surface 98. As best seen in FIG. 17, this results in substantially no radial step or the like between the inner surface 98 of outer tube 4 and the inner surface 60 of inner tube 6 at their junction point. Accordingly, a medical device inserted into the quiver will not catch on the walls at the junction of the two tubes. Preferably the diameter of surface 58 is chosen to be slightly larger than the diameter of the inner surface 98 at that location. This ensures that the portion 16 in contact with the inner surface 98 is in compression and bears relatively firmly against the inner surface 98. Since the medical instruments with which the device is used may well have body fluids upon them this also prevents or reduces the likelihood of leakage through the junction of the outer and inner tubes.

The junction thus presents, to the medical instrument(s) a substantially smooth surface against which the devices will not catch when being inserted or withdrawn.

It will be appreciated that the closed end of a tube need not be on the smallest diameter tube and instead may be on the largest diameter tube; in effect the open and closed ends may be swapped. Where three or more tubes are utilised it is not necessary that the tubes be progressively smaller. For example, a collapsible quiver with three tubes may be made with two end tubes substantially the same diameter and the central tube sized to either fit either within or around the two end tubes.

After use it is desirable that the quiver can be collapsed, so as to take up less volume in a waste receptacle. Referring to FIG. 16 it will be noted that the lower rib 64 is provided, in cross-section, with upper and lower faces 92 and 94. These surfaces have a radius of curvature but may be planar. Lower face 94 allows the rib 64 to more easily pass through reduced diameter portion 24 away from outer end. Upper face 94 allows the rib 64 to more easily pass through reduced diameter portion 24 toward the outer end, such as after use and when the device needs to be deliberately collapsed. Axial compression force on the two tubes 4, 6 will cause fingers 32 to ride up on face 92, so increasing the size of the opening and allowing the rib 64 and the inner tube 6 to move toward the end 20.

Figures 18, 19:
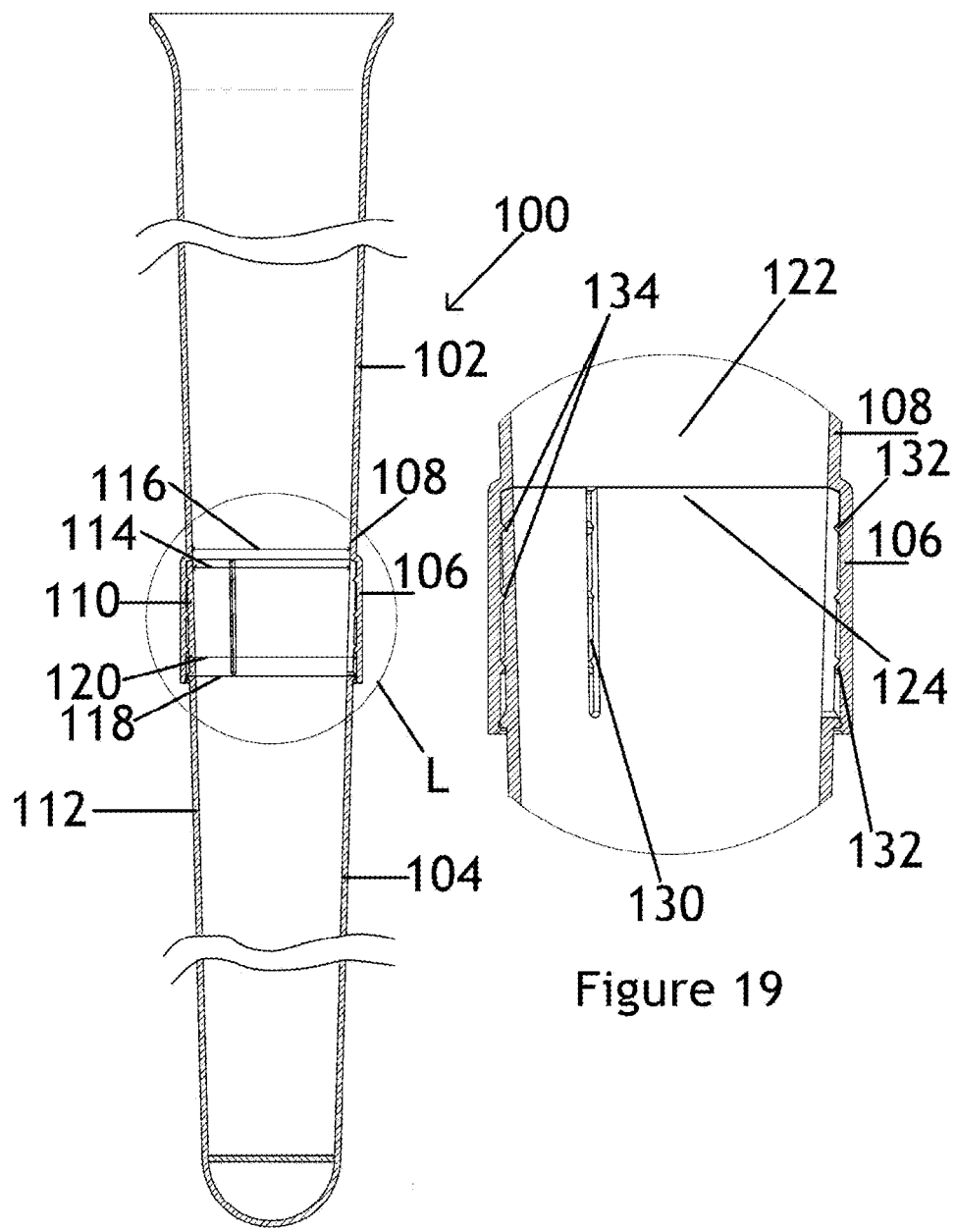
FIG. 18 is a sectional view of a quiver according to a second embodiment of the invention.
FIG. 19 is a detail sectional view of a part of the quiver of FIG. 18 circled L in FIG. 18.

Provision of a "step less" join between the two telescoping tubes may be achieved with other arrangements. FIGS. 18 and 19 show schematic cross-sectional of part of a collapsible quiver 100 comprised of outer tube 102 and inner tube 104. The outer tube 102 has inner portion 106 adjacent another portion 108.

The inner diameter of inner portion 106 is greater than that of adjacent portion 108. The inner tube has an outer portion 110 that has an inner diameter 114 that corresponds to inner diameter 116 of portion 108 and, preferably, an outer diameter 118 that corresponds to the inner diameter 120 of portion 106. Thus in the extended position the inner surfaces 122 and 124 of the outer and inner tubes present a substantially continuous surface.

The inner tube may be formed with an outside diameter substantially the same as that of the inside diameter of portion 108 with a transition between larger diameter portion 110 and smaller diameter portion 112. It will be appreciated that portion 110 will need to be of reduced diameter when in the storage position within small diameter portion 108 and accordingly one or more slots 130 may be provided to allow flexing inwards so as to reduce the effective diameter of the portion 110 and allow it to be located within smaller diameter portion 108.

The larger diameter portion 106 of outer tube may be provided with radially extending ribs, slots or grooves 132 and the outer portion 110 may be provided with complimentary slots, grooves or ribs 134. Providing ribs in outer tube 102 and slots or grooves in inner tube 104 does not increase the overall diameter of portion 110. The ribs may have an outer surface extending generally perpendicular to the axis, so as to lock the two tubes in the extended position and an angled inner face to allow the two tubes to be collapsed after use.

Whilst the invention has been described with reference to an embodiment havening tubular components with a substantially circular cross-section it will be appreciated that a circular cross-section is not essential to the invention and non-circular cross-sections may be used, such as oval, elliptical, polygonal or free form curve type cross-sections.

Unless the context clearly requires otherwise, throughout the description and any claims the words "comprise", "comprising", and the like are to be construed in an inclusive sense as opposed to an exclusive or exhaustive sense; that is to say, in the sense of "including, but not limited to".

The features of the invention described or mentioned in this document may be combined in any combination of features where features are not mutually exclusive.

It will be apparent to those skilled in the art that many obvious modifications and variations may be made to the embodiments described herein without departing from the spirit or scope of the invention.

The invention claimed is:

1. A collapsible medical quiver comprising
at least two elongate tubular members, comprising a first elongate tubular member and a second elongate tubular member;
the first member having a first member inner surface and a free end portion with a first open end;
the second member having a second member inner surface and a second member outer surface;
at least a part of the second member received within the first member for reciprocal motion in the elongate direction relative to the first member from a retracted position to an extended position in which at least a first end portion of the second member extends out of the first open end;
the second member having a second end portion at a second end thereof, the second end portion comprising a first inner surface portion and an outer surface portion and, in the extended position, the outer surface portion engages the first member inner surface, and
the first inner surface portion and the outer surface portion converge toward the second end so that, in the extended position, at the junction of the second end with the first member, the internal cross sectional area normal to the longitudinal axis of the first inner surface portion at the second end and the internal cross sectional area of the first member normal to the longitudinal axis are the same.

2. The collapsible medical quiver of claim 1 wherein the outer surface portion extends alongside the first member inner surface and the first inner surface portion extends toward the outer surface portion.

3. The collapsible medical quiver of claim 2 wherein, in longitudinal section, the first inner surface portion is curved.

4. The collapsible medical quiver of claim 1 wherein the first inner surface portion extends from a second inner surface portion of the second member inner surface.

5. The collapsible medical quiver of claim 4 wherein, in longitudinal section, the first inner surface portion extends tangent to the second inner surface portion.

6. The collapsible medical quiver of claim 1 wherein the first member inner surface and the second member outer surface are shaped so that movement of the second member from the retracted position to the extended position brings at least part of the outer surface portion of the second end portion and at least part of the first member inner surface into engagement or into closer engagement with each other.

7. The collapsible medical quiver of claim 1 wherein the outer surface portion engages the first member inner surface when the device is in the extended position to provide a seal that resists passage of fluid between the first and second members.

8. The collapsible medical quiver of claim 1 wherein the outer surface portion is sized so that the first member applies a compressive force to the second member when in the extended position.

9. The collapsible medical quiver of claim 1 wherein the second member has a first retaining portion and, when in the extended position, the first retaining portion is outside the first member adjacent the free end of the first member and resists movement of the second member toward the retracted position.

10. The collapsible medical quiver of claim 9 wherein the first retaining portion and the free end portion are sized so that passage of the first retaining portion through the free end portion requires deflection of at least a part of the free end portion.

11. The collapsible medical quiver of claim 9 wherein the second member has a second retaining portion and, when in the extended position, the second retaining portion engages with the first member and resists movement of the second member toward further extension.

12. The collapsible medical quiver of claim 11 wherein the first member has an intermediate portion between its first and second ends and the free end portion is connected to the adjacent intermediate portion by a transition portion and wherein, when in the extended position, the second retaining portion is located adjacent the transition portion.

13. The collapsible medical quiver of claim 12 wherein the free end portion has a cross sectional area normal to the longitudinal axis that is less than the cross sectional area normal to the longitudinal axis of the adjacent intermediate portion.

14. The collapsible medical quiver of claim 1 wherein the first member inner surface and the second member outer surface are shaped so that movement of the second member from the extended position to the retracted position brings at least part of the second member outer surface of the first end portion and at least part of the first member inner surface into engagement with each other.

15. A collapsible medical quiver comprising
at least two elongate tubular members, comprising a first elongate tubular member and a second elongate tubular member;
the first member having a first member inner surface and a free end portion with a first open end;
the second member (4) having a second member inner surface and a second member outer surface;
at least a part of the second member received within the first member for reciprocal motion in the elongate direction relative to the first member from a retracted position to an extended position in which at least a first end portion of the second member extends out of the first open end;
the second member having a second end portion at a second end thereof with a first inner surface portion and an outer surface portion and, in the extended position, the outer surface portion engages the first member inner surface;
the first inner surface portion and the outer surface portion converge toward the second end so that, in the extended position, at the junction of the second end with the first member, the internal cross sectional area normal to the longitudinal axis of the second end and the internal cross sectional area of the first member normal to the longitudinal axis are the same;
the first member inner surface and the outer surface portion are shaped so that movement of the second member from the retracted position to the extended position brings at least part of the second member outer surface and at least part of the first member inner surface into engagement or into closer engagement with each other;
wherein the second member outer surface portion engages the first member inner surface when the device is in the extended position to provide a seal that resists passage of fluid between the first member inner surface and second member outer surface.

16. The collapsible medical quiver of claim 15 wherein the second member outer surface portion is sized so that the first member applies a compressive force to the second member when in the extended position.

17. The collapsible medical quiver of claim 16 the first member has an intermediate portion between its first and second ends and the free end portion is connected to the adjacent intermediate portion by a transition portion.

18. The collapsible medical quiver of claim 17 wherein the second member has a second retaining portion that is located in the first member adjacent the transition portion when in the extended position.

19. The collapsible medical quiver of claim 18 wherein the free end portion has a cross sectional area normal to the longitudinal axis that is less than the cross sectional area normal to the longitudinal axis of the adjacent intermediate portion.

* * * * *